US007129299B2

(12) United States Patent
Detert et al.

(10) Patent No.: US 7,129,299 B2
(45) Date of Patent: Oct. 31, 2006

(54) SULPHONATED COMB POLYMERS HAVING A SELECTED LITHIUM/SODIUM RATIO AND PREPARATIONS INCLUDING SUCH POLYMERS

(75) Inventors: Marion Detert, Hamburg (DE); Andreas Koller, Hamburg (DE); Roman Morschhäuser, Mainz (DE)

(73) Assignee: Beiersdorf AG, Hamburg (DE)

( * ) Notice: Subject to any disclaimer, the term of this patent is extended or adjusted under 35 U.S.C. 154(b) by 107 days.

(21) Appl. No.: 10/826,669

(22) Filed: Apr. 16, 2004

(65) Prior Publication Data

US 2005/0113529 A1    May 26, 2005

Related U.S. Application Data

(63) Continuation of application No. 10/090,525, filed on Mar. 4, 2002, which is a continuation of application No. PCT/EP00/08526, filed on Aug. 31, 2000.

(30) Foreign Application Priority Data

Sep. 4, 1999   (DE)   ................................ 199 42 302

(51) Int. Cl.
C08F 8/34       (2006.01)
C08F 220/62     (2006.01)
C08F 20/10      (2006.01)
C11D 17/00      (2006.01)
C11D 3/37       (2006.01)

(52) U.S. Cl. ............................... 525/329.7; 525/329.8; 525/330.4; 525/346

(58) Field of Classification Search ............. 525/329.7, 525/329.8, 330.4, 346
See application file for complete search history.

(56) References Cited

U.S. PATENT DOCUMENTS 5,633,223 A * 5/1997 Vasudevan et al. ......... 510/303

6,255,274 B1   7/2001   Becherer et al.
7,026,408 B1   4/2006   Detert et al.

FOREIGN PATENT DOCUMENTS

| EP | 0 204 234 A2 | 5/1986 |
|---|---|---|
| EP | 0 204 234 B1 | 5/1986 |
| EP | 1 043 352 A2 | 3/2000 |
| EP | 1 048 287 A2 | 4/2000 |
| JP | 59 230057 A2 | 12/1984 |
| WO | WO 91/08281 | * 6/1991 |
| WO | WO-9108281 | * 6/1991 |
| WO | WO 99/45055 A1 | 9/1999 |

OTHER PUBLICATIONS

"Synthesis of A new Family of Comb Polymers with side chain esters and their films containing lithium trifluoromethane sulfonate", Jounal of Materials Chemistry, 4(4) pp. 599-604, 1994 by Takebe, Yasuo; Hochi, Kazuo; Matsuba, Tasushi; Shirota, Yasuhiko.*

"Synthesis of a New Family of Comb Polymers with sidechain Esters and their Films containing Lithium Trifluoromethane sulfonate"—Jounal of Materilas Chemistry, Takebe, Yasuo; Hochi, Kazuo; Matsuba, Tasushi; Shirota, Yasuhjko, vol 4(4), p. 599-604, 1994.*

Database WPI Section Ch, Week 198506 Derwent Publications Ltd., London, GB; AN 1985-035383 XP002148564 & JP 59 230057 A (Toagosei Chem Ind Ltd), Dec. 24, 1984, abstract.

* cited by examiner

*Primary Examiner*—David W. Wu
*Assistant Examiner*—Ives Wu
(74) *Attorney, Agent, or Firm*—Alston & Bird LLP

(57) ABSTRACT

Water-soluble and/or water-dispersible comb polymers comprising a polymer main chain and polyester side-arms which contain sulfonic acid groups and which are linked to the polymer main chain via ester groups, wherein said side-arms have been at least partially neutralized by sodium and lithium cations, wherein the molar ratio of lithium to sodium is between 0.1 and 50.

20 Claims, No Drawings

SULPHONATED COMB POLYMERS HAVING A SELECTED LITHIUM/SODIUM RATIO AND PREPARATIONS INCLUDING SUCH POLYMERS

This is a continuation of application Ser. No. 10/090,525, filed Mar. 4, 2002, which is a continuation of PCT/EP00/08526, filed Aug. 31, 2000, and also claims the benefit of German Priority Application No. 199 42 302.4, filed Sep. 4, 1999, all of which are incorporated by reference herein in their entirety.

The present invention relates to novel sulphonated comb polymers and to preparations comprising such sulphonated comb polymers. In particular, the present invention relates to hair cosmetic active ingredients and preparations for setting, shaping, strengthening and improving the structure of hair.

An attractive hairstyle is nowadays generally regarded as being an indispensable part of a groomed appearance. In this connection, current fashion trends mean that time and again hairstyles which are considered chic are those which, for many types of hair, can only be formed or maintained for a relatively long period using certain setting active ingredients.

For these reasons, for some time use has sometimes been made of haircare cosmetics which are intended to be washed out of the hair again following contact, and sometimes of those which are intended to remain in the hair. The latter can be formulated such that they serve not only to care for individual hairs, but also improve the appearance of the hairstyle overall, for example by imparting more fullness to the hair, fixing the hairstyle over a relatively long period or improving its ability to be styled.

The property of fullness is attributed to a hairstyle, for example, when, following treatment, the hair does not lie flat on the scalp and can be easily styled.

The property of volume is attributed to a hairstyle, for example, when, following treatment, the hair has fullness and bounce.

The property of body is attributed to a hairstyle, for example, when the hair retains its volume even under disruptive external influences.

Setting active ingredients, which are usually polymeric compounds, can be incorporated into customary hair cleansers or conditioners. In many cases it is, however, advantageous to apply them in the form of specific products such as hair setting compositions or hair sprays.

There have recently been a number of developments in the hair cosmetics field which have created a need for new types of setting active ingredients and new types of formulation. Many of these developments are based not on performance disadvantages or shortcomings of known compositions, but, for example, on environmental protection viewpoints, legal provisions or other "non-technical" reasons.

For example, efforts are increasing in particular to change over from compositions based on volatile organic compounds (abbreviation: VOCs), e.g. alcohols, to water-based compositions.

However, the prior art lacks active ingredients (polymers) and preparations which conform to the requirements given above. For example, the preparations of the prior art which fix hairstyles generally comprise constituents (synthetic or natural polymers) which run the risk, in cases where readily volatile organic constituents are partially or completely replaced by water, of experiencing significant impairment of the product properties, which often has to be compensated for by clever formulation. In addition, the fixing preparations of the prior art are frequently distinguished by formulation constituents which have insufficient long-term stability and which can only be formulated with difficulty or in a complex manner, this applying in particular to silicone derivatives, which are used to improve the flexibility and tactility of the polymer film surface.

It was therefore the object to develop appropriate compositions which, with regard to performance properties, for example spray behaviour and drying time in the case of hair sprays, satisfy the expectations imposed by the consumer, and at the same time have a reduced content of volatile organic compounds, without the elementary properties of the polymer film on the hair, such as, for example, clarity/tranparency, surface tactility, shine, elasticity and wash-off, being negatively influenced, and where the processability of the formulation constituents is simple and unproblematical.

It has now been found, and herein lies the basis of the solution to the problems, that water-soluble and/or water-dispersible comb polymers consisting of a polymer main chain and polyester side-arms which contain sulphonic acid groups and are linked to said polymer main chain via ester groups, which side-arms have been at least partially neutralized by sodium and lithium counterions, where the molar ratio of lithium to sodium is between 0.1 and 50, preferably between 0.5 and 25, overcome or at least reduce the disadvantages of the prior art.

The comb polymers according to the invention are distinguished both by good water and alcohol compatibility and by favourable film properties and high wetting ability. In addition, they are easy to formulate.

The basic structure of the comb polymers according to the invention essentially follows the scheme below:

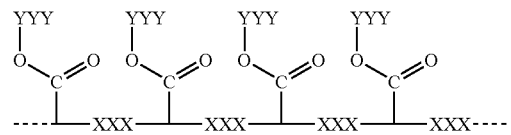

Here, the groups having the designation XXX bonded to one another are the basic component of a polymer backbone to which molecular groups are bonded via ester functions, said groups having the designation YYY. The molecular groups YYY are either the complete sulfonic acid group-containing polyester side-arms of the comb polymers according to the invention or else can be other molecular groups.

In this connection, the polymeric main chain of the comb polymers used according to the invention preferably consists of:

a) polymeric aliphatic, cycloaliphatic or aromatic polycarboxylic acids or derivatives thereof, such as, for example, polyacrylic acid, polymethacrylic acid and esters thereof (esters of the two acids with aliphatic, cycloaliphatic or aromatic alcohols with $C_1$ to $C_{22}$), maleic acid, maleic anhydride, fumaric acid and polynorbomenic acid. The number average molecular weights of the polycarboxylic acid used can be between 200 and 2,000,000 g/mol, the range 2000–100,000 g/mol being preferably used.

The polyester side chains are bonded via an ester group which is formed by the reaction of a functional group of the main chain (—COOH in the case of polycarboxylic acids or —OH in the case of polyalcohols) with a corresponding group of the polyester (OH in the case of polycarboxylic acids and COOH in the case of polyalcohols). It is of course also possible for reactive derivatives of the components listed above to be reacted (for example anhydrides, esters, halogen compounds and the like).

The polyesters used according to the invention can advantageously be distinguished by the following generic structural formulae:

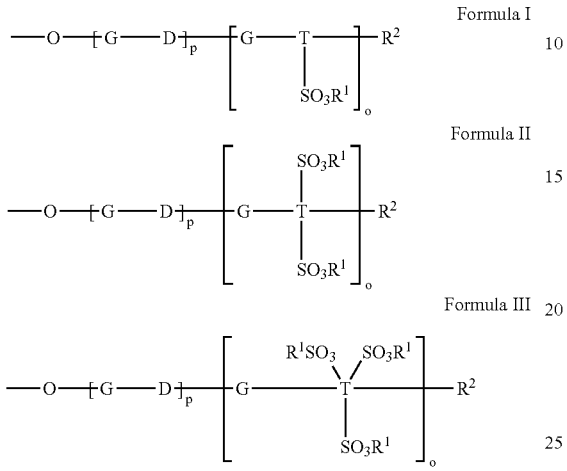

etc.

wherein p and o can be chosen such that the average molecular weights, referred to previously, of the main chain constituents used are achieved.

The polyester side chains according to formula I–III advantageously consist of:

G: an aromatic, aliphatic or cycloaliphatic organyl unit having a carbon number of from $C_2$ to $C_{22}$ and containing at least two terminal oxygen atoms, or derivatives of a polyglycol of the form $HO-[R^3-O]_k-[R^4-O]_m-H$, corresponding to an organyl unit

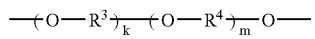

The radicals $R^3$ and $R^4$ are alkylene radicals having a carbon number of from $C_2$ to $C_{22}$, where the two radicals do not necessarily have to be different.

For the coefficients k and m the following applies: $k+m \geq 1$, where k and m can also be chosen such that the average molecular weights, referred to previously, of the main chain constituents used are achieved.

D: an aromatic, aliphatic or cycloaliphatic organyl unit having a carbon number of from $C_2$ to $C_{22}$ and containing at least two terminal acyl groups, where combinations of two or more different acid components may also be present in the claimed target molecule, for example an organyl unit of the scheme

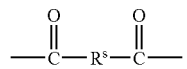

where $R^S$ can be aromatic and linear or cyclic, saturated or unsaturated aliphatic bifunctional radicals having carbon numbers of from $C_2$ to $C_{22}$.

T: a compound from the group of the sulphonated aromatic, aliphatic or cycloaliphatic organyl compounds containing at least two terminal acyl groups $R^1$: can be lithium and/or sodium as well as, where appropriate, further counterions, e.g. potassium, magnesium, calcium, ammonium, monoalkylammonium, dialkylammonium, trialkylammonium or tetraalkylammonium, in which the alkyl positions of the amines are, independently of one another, occupied by $C_1$ to $C_{22}$-alkyl radicals and 0 to 3 hydroxyl groups.

$R^2$: a molecular moiety chosen from the groups of aromatic, aliphatic or cycloaliphatic amino functions: ($-NH-R^5$, $-NR^5_2$, where $R^5$ can be an alkyl or aryl radical with $C_1$ to $C_{22}$)

aromatic, aliphatic or cycloaliphatic monocarboxylic acid groups: ($-COOR^6$, where $R^6$ is an alkyl or aryl radical with $C_1$ to $C_{200}$)

aromatic, aliphatic or cycloaliphatic organyl radicals bridged via ether functions:

polyalkoxy compounds bridging via ether functions and of the form $-O-[R^7-O]_q-[R^8-O]_r-Y$ The radicals $R^7$ and $R^8$ are advantageously alkyl radicals having a carbon number of from $C_2$ to $C_{22}$, where the two radicals do not necessarily have to be different. The radical Y can either be hydrogen or an aliphatic nature with $C_1-C_{22}$. For the coefficients q and r the following applies: $q+r \geq 1$.

mono- or polyethoxylated sulphonated organyl radicals bridging via ether functions, or preferably alkali metal or alkaline earth metal salts thereof, such as, for example, advantageously characterized by the generic structural formula $-(O-CH_2-CH_2)_s-SO_3R^1$ where $s \geq 1$, and where s can also be chosen such that the average molecular weights, referred to previously, of the main chain constituents used are achieved.

The functionality of the components used according to the invention is not of course limited to the use of OH groups, but also includes COOH end groups, or mixtures of the two, it also being the case here that at least two COOH groups must be freely present in the molecule. Reactive derivatives such as anhydrides, esters, epoxides or halides can of course also be used.

The number average molecular weights of the comb polymers according to the invention can advantageously be between 200 and 2,000,000 g/mol, particularly advantageously between 200 and 100,000 g/mol, the range 1000–30,000 g/mol being preferably used, very particularly advantageously 5000–15,000 g/mol.

The polyesters according to the invention are advantageously prepared by esterifying or transesterifying the parent functional alcohol components and diols with the carboxylic acids or suitable derivatives thereof (for example alkyl esters, halides and the like) in the presence of an esterification catalyst, such as alkali metal hydroxides, carbonates and acetates thereof, alkaline earth metal oxides, hydroxides, carbonates and acetates, and alkali metal and alkaline earth metal salts of fatty acids having 6 to 22 carbon atoms. Also suitable are titanium compounds, such as titanates, metallic tin and organic tin compounds, such as mono- and dialkyltin derivatives, as esterification catalysts. The esterification/transesterification is preferably carried out using tin powder or titanium tetraisopropoxide as catalyst.

The esterification/transesterification is preferably carried out at temperatures of from 120° C. to 280° C. the more readily boiling condensate (alcohols or water) forming being removed by distillation from the condensation product, preferably under reduced pressure up to <0.1 mbar.

Starting materials which can be used for the polyester backbone of comb polymers according to the invention are aliphatic, cycloaliphatic or aromatic polycarboxylic acids or derivatives thereof, such as, for example, polyacrylic acid, polymethacrylic acid and esters thereof (esters of the two acids with aliphatic, cycloaliphatic or aromatic alcohols with $C_1$ to $C_{22}$), maleic acid, maleic anhydride, fumaric acid and polynorbornenic acid. The number average molecular weights of the individual polycarboxylic acids can be between 200 and 2,000,000 g/mol, the range 2000–100,000 g/mol being preferably used.

Random or block copolymers of the abovementioned class of compound with other vinylic monomers such as, for example, styrene, acrylamide, α-methylstyrene, styrene, N-vinylpyrrolidone, N-vinylcaprolactone, acrylamidopropylenesulphonic acid and the alkali, alkaline earth and ammonium salts thereof, MAPTAC (meth-acrylamidopropyltrimethylammonium chloride), DADMAC, vinylsulphonic acid, vinylphosphonic acid, crotonic acid, vinylacetamide, vinylmethylacetamide, vinylformamide, acrylic acid or methacrylic acid derivatives (for example free acid or ester), or acrylamide derivatives or vinyl acetate can also be used to form the polymeric main chain.

As the basis for aromatic, aliphatic or cycloaliphatic organyl units having a carbon number of from $C_2$ to $C_{22}$ and containing at least two terminal oxygen atoms, or derivatives of a polyglycol of the form $HO-[R^3-O]_k-[R^4-O]_m-H$, it is possible to use bifunctional alcohol components.

Particularly suitable for this purpose are at least difunctional aromatic, aliphatic or cycloaliphatic alcohols having a carbon number from $C_2$ to $C_{22}$ or a polyglycol of the form $HO-[R^3-O]_k-[R^4-O]_m-H$. The radicals $R^3$ and $R^4$ are alkyl radicals having a carbon number from $C_2$ to $C_{22}$, where the two radicals can be identical or different. For the coefficients k and m the following applies: $k+m \geq 1$, where k and m can also be chosen such that the average molecular weights, referred to previously, of the main chain constituents used are achieved.

It can be of particular advantage to use tri-, tetra- or, generally, polyfunctional alcohol components instead of difunctional alcohol components, advantageously chosen, for example, from the group below:

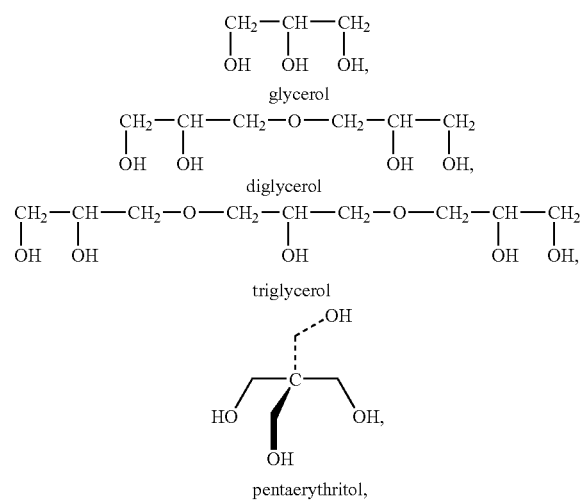

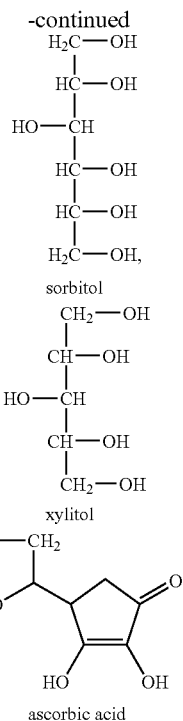

As the basis for aromatic, aliphatic or cycloaliphatic organyl units having a carbon number of from $C_2$ to $C_{22}$ and containing at least two terminal acyl groups, for example organyl units of the scheme

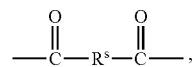

it is possible to use, for example, aromatic and linear or cyclic, saturated or unsaturated aliphatic carboxylic acids having a carbon number of from $C_2$ to $C_{22}$ or anhydrides thereof, for example phthalic acid, isophthalic acid, naphthalenedicarboxylic acid, cyclohexanedicarboxylic acid, adipic acid, succinic acid, glutaric acid, pimelic acid, suberic acid, azelaic acid, sebacic acid, brassylic acid. Combinations of two or more different acid components are also possible as monomer unit in the claimed target molecule.

Suitable sulfonic acid group-containing monomers are sulphonated aromatic, aliphatic or cycloaliphatic dialcohols, diacids or esters thereof, such as, for example, sulphosuccinic acid, 5-sulphoisophthalic acid or alkali metal or alkaline earth metal salts or mono-, di-, tri- or tetraalkylammonium salts thereof containing $C_1$ to $C_{22}$-alkyl radicals. Of the alkali metal salts, particular preference is given to lithium and sodium salts.

Use is also made of aromatic, aliphatic or cycloaliphatic amines with $C_1$ to $C_{22}$-alkyl or aryl radicals and/or aromatic, aliphatic or cycloaliphatic monocarboxylic acids with $C_1$ to $C_{200}$-alkyl or aryl radicals and/or polyalkoxy compounds of the form $-O-[R^7-O]_q-[R^8-O]_r-X$, where the radicals $R^7$ and $R^8$ are alkyl radicals, which may be identical or different, are a carbon number of from $C_2$ to $C_{22}$, and the radical X can either by hydrogen or of an aliphatic nature with $C_1-C_{22}$, and the coefficients q and r are: $q+r \geq 1$.

Likewise suitable are sulphonated mono- or polyethylene glycols or, preferably, alkali metal or alkaline earth metal salts thereof: $(H-(O-CH_2-CH_2)_s-SO_3R^1$ where $s \geq 1$, where s can also be chosen such that the average molecular weights, referred to previously, of the main chain constituents used are achieved.

To prepare the polyesters according to the invention, the alcohols and acids or esters used to form the side chain are advantageously used in the molar ratios from 1:1 to about 10:1 (1 or 10 parts of di- or polyol), and the alcohol and water which form, and the excess component are removed by distillation after condensation has taken place. Alcohol and acid components are preferably present in the target molecule in the approximate stoichiometric ratio 1:1.

The proportion of acid components containing sulphonic acid radicals is 1 to 99 mol %, preferably 10 to 40 mol %, particularly preferably 15 to 25 mol %, based on the total amount of carboxylic acids.

The polyesters of the general formula I which contain sulfonic acid groups have very favourable performance properties if the diol components used are 1,2-propanediol and/or diethylene glycol and/or cyclohexanedimethanol, if the carboxylic acids used are isophthalic acid, also with 1,3-cyclohexanedicarboxylic acid or also with 2,6-naphthalenedicarboxylic acid or also with adipic acid, and if the sulpho group-containing radicals used are the sodium and/or lithium salt of 5-sulphoisophthalic acid or the sodium and/or lithium salt of isethionic acid.

A section from a comb polymer molecule according to the invention is given below, a polyacrylic acid chain forming the backbone of the comb polymer molecule. The acid functions have been esterified with polyols, which for their part have been esterified with an acid function of isophthalic acid molecules. Further polyols from which structural elements of this polymer molecule are derived are pentaerythritol and 1,2-propanediol. The sulphonate group-containing agent from which structural elements of the polymer molecule are derived is, for example, the sodium and/or lithium salt of a 5-sulphoisophthalic dialkyl ester.

For reasons of reaction control, which are known to the person skilled in the art, no absolute uniformity of substitution prevails in the target polymer; instead, a certain random distribution breadth of substitution is to be assumed. In addition, certain reactive molecular groups will also be observed crosslinking two or more polymer chains to give a more or less complex network, as the molecular scheme below also attempts to show.

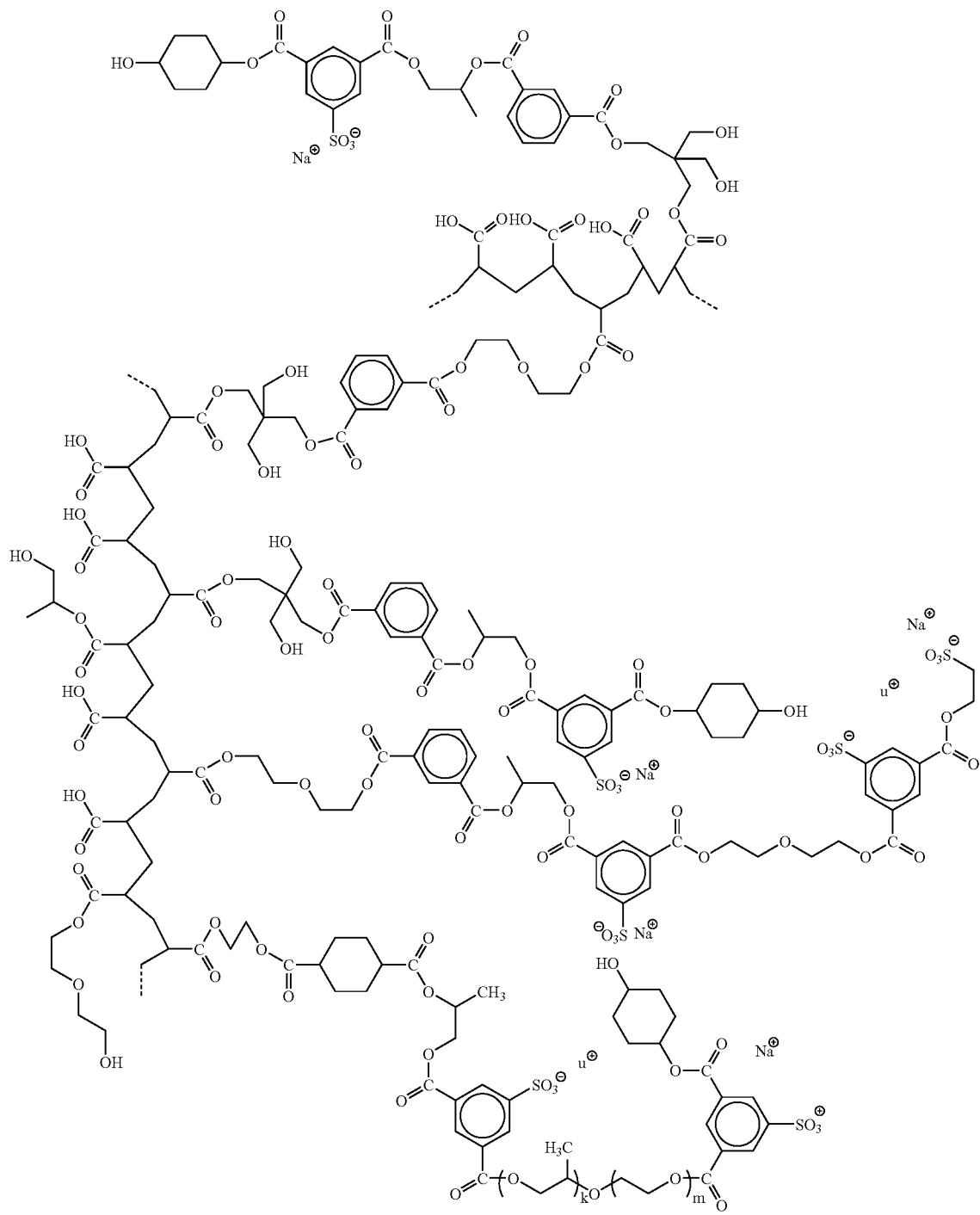

The sulfonic acid-containing polyesters to be used according to the invention are colourless to yellowish, odour-neutral solids. They are readily soluble in water and alcohols. They can advantageously be incorporated into cosmetic preparations for setting hair.

The comb polymers according to the invention are advantageously prepared by mixing one or more polyfunctional alcohols with a substance which contains sulphonic acid groups and at least two carboxyl groups, for example sodium dimethyl 5-sulphoisophthalate, optionally a further substance containing at least two carboxyl groups, and a polymer, with one or more polycarboxylic acids, for example polyacrylic acid or polymethacrylic acid, heating the mixture and subjecting it to customary work-up steps.

In a particular embodiment of the present invention, the water-soluble and/or water-dispersible comb polymers according to the invention, consisting of a polyacrylic acid-containing polymer main chain and sulfonic acid group-containing polyester side-arms, are therefore incorporated into cosmetic, in particular hair cosmetic, preparations.

For use, the cosmetic and dermatological preparations according to the invention are applied to the hair in a sufficient amount in the manner customary for cosmetics.

The cosmetic and dermatological preparations according to the invention can comprise cosmetic auxiliaries, as are customarily used in such preparations, e.g. preservatives, bactericides, perfumes, antifoams, dyes, pigments which have a colouring action, thickeners, surface-active substances, emulsifiers, emollients, moisturizers and/or humectants, fats, oils, waxes or other customary constituents of a cosmetic or dermatological formulation, such as alcohols, polyols, polymers, foam stabilizers, electrolytes, organic solvents or silicone derivatives.

In cosmetic preparations for setting hair, such as, for example, hair sprays, hair lacquers, setting foams, setting liquids, styling gels etc., the comb polymers to be used according to the invention may preferably be used in concentrations of from 0.5 to 30 per cent by weight.

The hair-setting compositions according to the invention can be in the form of hair sprays or foam aerosols, and comprise the additives which are customary for this purpose and which correspond to the prior art, provided there is corresponding compatibility. These are, for example, further solvents, such as lower polyalcohols and toxicologically acceptable ethers and esters thereof, emollients, readily and poorly volatile silicones, readily and poorly volatile branched or unbranched hydrocarbons, emulsifiers, antioxidants, waxes, stabilizers, pH regulators, dyes, bodying agents, antistats, UV absorbers, perfumes, etc.

If the composition according to the invention is to be used as hair spray or foam aerosol, then a propellant is normally added. Customary propellants are lower alkanes, for example propane, butane or isobutane, dimethyl ether, nitrogen, nitrogen dioxide or carbon dioxide or mixtures of these substances.

In the case of use in mechanical spraying or foaming devices, for example spray pumps or manual foam pumps or squeeze systems, the propellant can usually be omitted.

The aqueous preparations according to the invention optionally advantageously comprise alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol and, in particular, one or more thickeners, which can be advantageously chosen from the group consisting of silicon dioxide, aluminium silicates, polysaccharides and derivatives thereof, e.g. hyaluronic acid, xanthan gum, hydroxypropylmethylcellulose, particularly advantageously from the group of polyacrylates, preferably a polyacrylate from the group of Carbopols, for example Carbopols of grades 980, 981, 1382, 2984, 5984, in each case individually or in combination.

In the technical sense, the term gels means: relatively dimensionally stable, readily deformable disperse systems of at least two components which as a rule consist of a—in most cases solid—colloidally dispersed substance of long-chain molecular groups (e.g. gelatine, silica, polysaccharides) as the backbone-former and a liquid dispersing agent (e.g. water). The colloidally disperse substance is often referred to as a thickener or gelling agent. It forms a three-dimensional network in the dispersing agent, it being possible for individual particles present in colloidal form to be linked to one another more or less firmly via electrostatic interaction. The dispersing agent, which surrounds the network, is distinguished by electrostatic affinity for the gelling agent, i.e. a predominantly polar (in particular: hydrophilic) gelling agent preferably gels a polar dispersing agent (in particular: water), whereas a predominantly nonpolar gelling agent preferably gels nonpolar dispersing agents.

Strong electrostatic interactions, which are realized, for example, in hydrogen bridge bonds between gelling agent and dispersing agent, but also between dispersing agent molecules amongst themselves, can lead to a high degree of crosslinking of the dispersing agent as well. Hydrogels can consist of virtually 100% of water (in addition, for example, to about 0.2–1.0% of a gelling agent) and have an entirely solid consistency. The water content is present here in ice-like structural elements, meaning that gels therefore do justice to the origin of their name [from Lat. "gelatum"="frozen" via the alchemistic term "gelatina" ($16^{th}$ century) for the modem term "gelatin"].

Gels according to the invention usually comprise alcohols of low carbon number, e.g. ethanol, isopropanol, 1,2-propanediol, glycerol and water in the presence of a thickener, which in the case of oily-alcoholic gels is preferably silicon dioxide or an aluminium silicate, and in the case of aqueous-alcoholic or alcoholic gels is preferably a polyacrylate.

The cosmetic and dermatological preparations according to the invention can, for example, also be shampoos, preparations for blow-drying or arranging hair, colouring preparations, or a styling or treatment lotion.

Preparations according to the invention can optionally advantageously be distinguished by a content of surfactants. Surfactants are amphiphilic substances which are able to dissolve organic nonpolar substances in water. As a result of their specific molecular structure having at least one hydrophilic and one hydrophobic molecular moiety, they are able to reduce the surface tension of water, wet the skin, facilitate soil removal and dissolution, facilitate rinsing and—if desired—control foaming.

The hydrophilic moieties of a surfactant molecule are mostly polar functional groups, for example $-COO^-$, $-OSO_3^{2-}$, $-SO_3^-$, while the hydrophobic moieties are usually nonpolar hydrocarbon radicals. Surfactants are generally classified according to the type and charge of the hydrophilic molecular moiety. In this connection, it is possible to differentiate between four groups:

anionic surfactants, cationic surfactants, amphoteric surfactants and nonionic surfactants.

Anionic surfactants usually have, as functional groups, carboxylate, sulphate or sulphonate groups. In aqueous solution, they form negatively charged organic ions in acidic or neutral media. Cationic surfactants are characterized almost exclusively by the presence of a quaternary ammonium group. In aqueous solution they form positively charged organic ions in acidic or neutral media. Amphoteric surfactants contain both anionic and cationic groups and accordingly in aqueous solution exhibit the behaviour of anionic or cationic surfactants depending on the pH. In strongly acidic media they have a positive charge, and in alkaline medium a negative charge. By contrast, in the neutral pH range, they are zwitterionic, as the example below serves to illustrate:

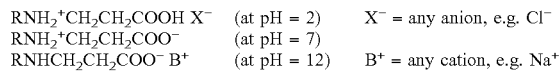

| | | |
|---|---|---|
| RNH$_2^+$CH$_2$CH$_2$COOH X$^-$ | (at pH = 2) | X$^-$ = any anion, e.g. Cl$^-$ |
| RNH$_2^+$CH$_2$CH$_2$COO$^-$ | (at pH = 7) | |
| RNHCH$_2$CH$_2$COO$^-$ B$^+$ | (at pH = 12) | B$^+$ = any cation, e.g. Na$^+$ |

Polyether chains are typical of nonionic surfactants. Nonionic surfactants do not form ions in an aqueous medium.

A. Anionic Surfactants

Anionic surfactants which can be used advantageously are acylamino acids (and salts thereof), such as
1. acyl glutamates, for example sodium acyl glutamate, di-TEA-palmitoyl aspartate and sodium caprylic/capric glutamate,
2. acylpeptides, for example palmitoyl-hydrolysed milk protein, sodium cocoyl-hydrolysed soya protein and sodium/potassium cocoyl-hydrolysed collagen,
3. sarcosinates, for example myristoyl sarcosinate, TEA-lauroyl sarcosinate, sodium lauroyl sarcosinate and sodium cocoyl sarcosinate,
4. taurates, for example sodium lauroyl taurate and sodium methylcocoyl taurate,
5. acyl lactylates, lauroyl lactylate, caproyl lactylate
6. alaninates carboxylic acids and derivatives, such as
1. carboxylic acids, for example lauric acid, aluminium stearate, magnesium alkanolate and zinc undecylenate,
2. ester carboxylic acids, for example calcium stearoyl lactylate, laureth-6 citrate and sodium PEG-4 lauramide carboxylate,
3. ether carboxylic acids, for example sodium laureth-13 carboxylate and sodium PEG-6 cocamide carboxylate, Phosphoric esters and salts, such as, for example, DEA-oleth-10 phosphate and dilaureth-4 phosphate, sulphonic acids and salts, such as
1. acyl isethionates, e.g. sodium/ammoniumcocoyl isethionate,
2. alkylarylsulphonates,
3. alkylsulphonates, for example sodium cocomonoglyceride sulphate, sodium $C_{12-14}$-olefin sulphonate, sodium lauryl sulphoacetate and magnesium PEG-3 cocamide sulphate,
4. sulphosuccinates, for example dioctyl sodium sulphosuccinate, disodium laureth sulphosuccinate, disodium lauryl sulphosuccinate and disodium undecyleneamido-MEA sulphosuccinate and sulphuric esters, such as
1. alkyl ether sulphates, for example sodium, ammonium, magnesium, MIPA, TIPA laureth sulphate, sodium myreth sulphate and sodium $C_{12-13}$ pareth sulphate,
2. alkyl sulphates, for example sodium, ammonium and TEA lauryl sulphate.

B. Cationic Surfactants

Cationic surfactants which can optionally be used advantageously are
1. alkylamines,
2. alkylimidazoles,
3. ethoxylated amines and
4. quaternary surfactants,
5. ester quats Quaternary surfactants contain at least one N atom which is covalently bonded to 4 alkyl or aryl groups. Irrespective of the pH, this leads to a positive charge. Alkylbetaine, alkylamidopropylbetaine and alkylamidopropylhydroxysultaine are advantageous. The cationic surfactants used according to the invention can also preferably be chosen from the group of quaternary ammonium compounds, in particular benzyltrialkylammonium chlorides or bromides, such as, for example, benzyldimethylstearylammonium chloride, and also alkyltrialkylammonium salts, for example cetyltrimethylammonium chloride or bromide, alkyldimethylhydroxyethylammonium chlorides or bromides, dialkyldimethylammonium chlorides or bromides, alkylamidoethyltrimethylammonium ether sulphates, alkylpyridinium salts, for example lauryl- or cetylpyridinium chloride, imidazoline derivatives and compounds having cationic character, such as amine oxides, for example alkyldimethylamine oxides or alkylaminoethyldimethylamine oxides. In particular the use of cetyltrimethylammonium salts is advantageous.

C. Amphoteric Surfactants

Amphoteric surfactants which can be used advantageously are
1. acyl/dialkylethylenediamine, for example sodium acyl amphoacetate, disodium acyl amphodipropionate, disodium alkyl amphodiacetate, sodium acyl amphohydroxypropylsulphonate, disodium acyl amphodiacetate and sodium acyl amphopropionate,
2. N-alkylamino acids, for example aminopropylalkylglutamide, alkylaminopropionic acid, sodium alkylimidodipropionate and lauroamphocarboxyglycinate.

D. Nonionic Surfactants

Nonionic surfactants which can be used advantageously are
1. alcohols,
2. alkanolamides, such as cocamides MEA/DEA/MIPA,
3. amine oxides, such as cocoamidopropylamine oxide,
4. esters which are formed by esterification of carboxylic acids with ethylene oxide, glycerol, sorbitol or other alcohols,
5. ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glycoside and cocoglycoside.
6. sucrose esters, sucrose ethers
7 polyglycerol esters, diglycerol esters, monoglycerol esters
8. methylglucose esters, esters of hydroxy acids Also advantageous is the use of a combination of anionic and/or amphoteric surfactants with one or more nonionic surfactants.

For the purposes of the present invention, the use of anionic, amphoteric and/or nonionic surfactants is generally preferable over the use of cationic surfactants.

The cosmetic and dermatological preparations optionally comprise active ingredients and auxiliaries as are customarily used for this type of preparation for hair care and hair treatment. Auxiliaries used are preservatives, surface-active substances, antifoams, thickeners, emulsifiers, fats, oils, waxes, organic solvents, bactericides, perfumes, dyes or pigments, the objective of which is to colour the hair or the cosmetic or dermatological preparation itself, electrolytes, and substances to counteract greasiness in hair.

For the purposes of the present invention, the term electrolytes means water-soluble alkali metal, ammonium, alkaline earth metal (including magnesium) and zinc salts of inorganic anions and any mixtures of such salts, when it has to be ensured that these salts are distinguished by pharmaceutical or cosmetic acceptability.

The anions according to the invention are preferably chosen from the group of chlorides, sulphates and hydrogensulphates, phosphates, hydrogenphosphates and linear and cyclic oligophosphates, and carbonates and hydrogencarbonates.

Cosmetic preparations which are shampoos preferably comprise at least one anionic, nonionic or amphoteric surface-active substance, or else mixtures of such substances in the aqueous medium and auxiliaries as are customarily used therefor. The surface-active substance or the mixtures of these substances can be present in the shampoo in a concentration between 1% by weight and 50% by weight.

A cosmetic preparation in the form of a lotion which is not rinsed out, in particular a lotion for arranging hair, a lotion used during the blow-drying of hair, a styling and treatment lotion, is generally an aqueous, alcoholic or aqueous-alcoholic solution and comprises the comb polymers according to the invention.

The compositions according to the invention optionally comprise the additives customary in cosmetics, for example perfume, thickeners, dyes, deodorants, antimicrobial substances, refatting agents, complexing agents and sequestering agents, pearlizing agents, plant extracts, vitamins, active ingredients and the like.

The examples below serve to illustrate the present invention without limiting it. Unless stated otherwise, all amounts, proportions and percentages are based on the weight and the total amount or on the total weight of the preparations.

(A) PREPARATION EXAMPLES

Preparation Example 1

| Starting material | Mass (g) |
| --- | --- |
| Isophthalic acid | 265.81 |
| 5-Sulfoisophthalic methyl ester, Na salt | 100.52 |
| 5-Sulfoisophthalic acid, Li salt | 22.92 |
| Isethionic acid, Na salt | 10.96 |
| Polyacrylic acid ($M_n$ = 2000 g/mol) | 3.00 |
| Sodium carbonate | 0.60 |
| Titanium tetraisopropoxide | 0.60 |
| 1,2-Propanediol | 195.40 |
| Diethylene glycol | 166.95 |

Preparation Method:

A 2 L four-necked flask fitted with precision-ground stirrer, internal thermometer, gas inlet pipe and distillation bridge is charged with 1,2-propanediol, diethylene glycol, 5-sulfoisophthalic methyl ester Na salt, 5-sulfoisophthalic acid Li salt, sodium carbonate and titanium tetraisopropoxide, and the mixture is transesterified at 180° C. for 5 hours. The methanol and water of reaction which form in the process are distilled off at atmospheric pressure. The sodium salt of isethionic acid, isophthalic acid and polyacrylic acid are then added to the reaction mixture, which is then rendered thoroughly inert with $N_2$. The reaction mixture is then heated slowly to 220° C. and held at this temperature until no further condensate distills over. Then, over a period of 3 hours, starting from atmospheric pressure, the internal pressure of the reaction vessel is reduced to oil pump vacuum. After a further 60 minutes, $N_2$ is admitted and the hot polymer melt is discharged.

Preparation Example 2

| Starting material | Mol (mmol) |
| --- | --- |
| 1,3-Cyclohexanedicarboxylic acid | 132.80 |
| Terephthalic dimethyl ester | 95.12 |
| 5-Sulfoisophthalic methyl ester, Na salt | 75.20 |
| 5-Sulfoisophthalic acid, Li salt | 75.20 |
| Polyacrylic acid ($M_n$ = 5000 g/mol) | 7.00 |
| Sodium carbonate | 0.60 |
| Titanium tetraisopropoxide | 0.80 |
| 1,2-Propanediol | 195.40 |
| Diethylene glycol | 166.95 |

Preparation Method:

A 2 L four-necked flask fitted with precision-ground stirrer, internal thermometer, gas inlet tube and distillation bridge is charged with 1,2-propanediol, diethylene glycol, 5-sulfoisophthalic methyl ester Na salt, 5-sulfoisophthalic acid Li salt, sodium carbonate and titanium tetraisopropoxide, and the mixture is transesterified at 180° C. for 5 hours. The methanol and water of reaction which form in the process are distilled off at atmospheric pressure. The sodium salt of isethionic acid, 1,3-cyclohexanedicarboxylic acid and polyacrylic acid are then added to the reaction mixture, which is then rendered thoroughly inert with $N_2$. The reaction mixture is then heated slowly to 220° C. and held at this temperature until no further condensate distills over. Then, over a period of 3 hours, starting from atmospheric pressure, the internal pressure of the reaction vessel is reduced to oil pump vacuum. After a further 60 minutes, $N_2$ is admitted and the hot polymer melt is discharged.

Preparation Example 3

| Starting material | Mass (g) |
| --- | --- |
| 2,6-Naphthalenedicarboxylic acid | 172.95 |
| 5-Sulfoisophthalic methyl ester, Na salt | 55.52 |
| 5-Sulfoisophthalic acid, Li salt | 97.13 |
| Isophthalic acid | 55.00 |
| Poly[acrylic acid-co-methacrylic acid methyl ester] $M_n$ = 5000 g/mol)* | 3.00 |
| Sodium carbonate | 0.60 |
| Titanium tetraisopropoxide | 0.60 |
| 1,2-Propanediol | 188.40 |
| Diethylene glycol | 155.12 |

Preparation Method:

A 2 L four-necked flask fitted with precision-ground stirrer, internal thermometer, gas inlet tube and distillation bridge is charged with 1,2-propanediol, diethylene glycol, 5-sulfoisophthalic methyl ester Na salt, 5-sulfoisophthalic acid Li salt, sodium carbonate and titanium tetraisopropoxide, and the mixture is transesterified at 180° C. for 5 hours. The methanol and water of reaction which form in the process are distilled off at atmospheric pressure. 2,6-Naphthalenedicarboxylic acid, isophthalic acid and poly[acrylic acid-co-methacrylic acid methyl ester] are then added to the reaction mixture, which is then rendered thoroughly inert with $N_2$. The reaction mixture is then heated slowly to 220° C. and held at this temperature until no further condensate distills over. Then, over a period of 3 hours, starting from atmospheric pressure, the internal pressure of the reaction vessel is reduced to oil pump vacuum. After a further 75 minutes, $N_2$ is admitted and the hot polymer melt is discharged.

Preparation Example 4

| Starting material | Mol (mmol) |
|---|---|
| Adipic acid | 172.95 |
| 5-Sulfoisophthalic methyl ester, Na salt | 55.52 |
| 5-Sulfoisophthalic acid, Li salt | 97.13 |
| Isophthalic acid | 55.00 |
| Polyacrylic acid ($N_n$ = 5000 g/mol) | 3.00 |
| Sodium carbonate | 0.60 |
| Titanium tetraisopropoxide | 0.60 |
| Diethylene glycol | 400.00 |

Preparation Method:

A 2 L four-necked flask fitted with precision-ground stirrer, internal thermometer, gas inlet tube and distillation bridge is charged with diethylene glycol, 5-sulfoisophthalic methyl ester Na salt, 5-sulfoisophthalic acid Li salt, sodium carbonate, titanium tetraisopropoxide, isophthalic acid, polyacrylic acid and adipic acid, and the mixture is slowly heated to 200° C. The methanol and water of reaction which form in the process are distilled off at atmospheric pressure. The mixture is then rendered adequately inert with $N_2$ and the reaction mixture is slowly heated to 250° C. and maintained at this temperature until no more condensate distills over. Then, over a period of 3 hours, starting from atmospheric pressure, the internal pressure of the reaction vessel is reduced to oil pump vacuum. After a further 75 minutes, $N_2$ is admitted and the hot polymer melt is discharged.

Preparation Example 5

| Starting material | Mol (mmol) |
|---|---|
| 1,4-Cyclohexanedicarboxylic acid | 172.95 |
| 5-Sulfoisophthalic methyl ester, Na salt | 55.52 |
| 5-Sulfoisophthalic acid, Li salt | 97.13 |
| Isophthalic acid | 55.00 |
| Polyacrylic acid ($M_n$ = 5000 g/mol) | 3.00 |
| Cyclohexanedimethanol | 150.12 |
| Sodium carbonate | 0.60 |
| Titanium tetraisopropoxide | 0.60 |
| Diethylene glycol | 400.00 |

Preparation Method:

A 2 L four-necked flask fitted with precision-ground stirrer, internal thermometer, gas inlet tube and distillation bridge is charged with cyclohexanedimethanol, diethylene glycol, 5-sulfoisophthalic methyl ester Na salt, 5-sulfoisophthalic acid Li salt, sodium carbonate, titanium tetraisopropoxide, isophthalic acid, polyacrylic acid and 1,4-cyclohexanedicarboxylic acid, and the mixture is slowly heated to 200° C. The methanol and water of reaction which form in the process are distilled off at atmospheric pressure. The mixture is then rendered sufficiently inert with $N_2$ and the reaction mixture is slowly heated to 250° C. and held at this temperature until no more condensate distills over. Then, over a period of three hours, starting from atmospheric pressure, the internal pressure of the reaction vessel is reduced to oil pump vacuum. After a further 75 minutes, $N_2$ is admitted and the hot polymer melt is discharged.

Preparation Example 6

| Starting material | Mass (g) |
|---|---|
| Pentaerythritol | 7.20 |
| 5-Sulfoisophthalic acid methyl ester, Na salt | 15.02 |
| 5-Sulfoisophthalic acid, Li salt | 140.21 |
| Isophthalic acid | 55.00 |
| Isethionic acid, Li salt | 25.98 |
| Polyacrylic acid ($M_n$ = 12,000 g/mol) | 3.00 |
| Sodium carbonate | 0.60 |
| Titanium tetraisopropoxide | 0.60 |
| 1,4-Cyclohexanedimethanol | 144.21 |
| Diethylene glycol | 400.00 |

Preparation Method:

A 2 L four-necked flask fitted with precision-ground stirrer, internal thermometer, gas inlet tube and distillation bridge is charged with diethylene glycol, 5-sulfoisophthalic methyl ester Na salt, 5-sulfoisophthalic acid Li salt, sodium carbonate, titanium tetraisopropoxide, isophthalic acid and pentaerythritol, and the mixture is slowly heated to 200° C. The methanol and water of reaction which form during the reaction are distilled off at atmospheric pressure. The polyacrylic acid and the isethionic acid Li salt are then added to the reaction mixture. The mixture is then rendered sufficiently inert with $N_2$ and the reaction mixture is slowly heated to 250° C. and held at this temperature until no more condensate distills over. Then, over a period of three hours, starting from atmospheric pressure, the internal pressure of the reaction vessel is reduced to oil pump vacuum. After a further 75 minutes, $N_2$ is admitted and the hot polymer melt is discharged.

(B) FORMULATION EXAMPLES

Hair Sprays

Examples 1–6

|  | Aerosol hair spray strong hold | | Aerosol hair spray extra strong hold |
|---|---|---|---|
|  | 1 | 2 | 3 |
| Polyester according to Preparation Example 1 | 8.00 | 8.00 | 10.00 |
| Ethanol | 40.00 | 25.00 | 25.00 |
| Perfume, care active ingredients, pH regulators, preservatives, solubilizers, corrosion inhibitors | q.s. | q.s. | q.s. |
| Dimethyl ether | 40.00 | 30.00 | 30.00 |
| Water, demin. | | ad 100.00 | |

|  | Aerosol care hair spray | Nonaerosol hair spray extra strong hold |
|---|---|---|

-continued

|  | 4 | 5 | 6 |
|---|---|---|---|
| Polyester according to Preparation Example 2 | 8.00 | 10.00 | 10.00 |
| Ethanol | 40.00 | — | 55.00 |
| Perfume, care active ingredients, pH regulators, preservatives, solubilizers, corrosion inhibitors | q.s. | q.s. | q.s. |
| Dimethyl ether | 40.00 | — | — |
| Water, demin. | ad 100.00 | | |

Setting Foam

Examples 7–8

|  | Setting foam strong hold 7 | Setting foam extra strong hold 8 |
|---|---|---|
| Polyester according to Preparation Example 3 | 8.00 | 10.00 |
| Cocamidopropylbetaine | 0.50 | 0.50 |
| Perfume, preservatives, pH regulators, solubilizers, | q.s. | q.s. |
| Propane/butane | 8.00 | 8.00 |
| Water, demin. | ad 100.00 | |

Styling Gels

Examples 9–10

|  | Styling gel strong hold 9 | Styling gel extra strong hold 10 |
|---|---|---|
| Polyester according to Preparation Example 4 | 8.00 | 10.00 |
| Carbomer | 0.50 | 0.50 |
| Perfume, preservatives, neutralizing agents, solubilizers, | q.s. | q.s. |
| Propylene glycol | 5.00 | 5.00 |
| Water, demin. | ad 100.00 | |

Styling Shampoos

Examples 11–12

| | Pearlescent styling shampoo | |
|---|---|---|
| | 11 | 12 |
| Polyester according to Preparation Example 5 | 5.00 | 5.00 |
| Sodium laureth sulphate | 11.00 | 11.00 |
| Cocamidopropylbetaine | 2.50 | 2.50 |
| Glycol distearate | 2.00 | — |

-continued

| | Pearlescent styling shampoo | |
|---|---|---|
| | 11 | 12 |
| Perfume, preservatives, pH regulators, solubilizers | q.s. | q.s. |
| Dimethicone copolyol | 0.50 | 0.50 |
| Water, demin. | ad 100.00 | |

Adjust pH to 6.0

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A comb polymer that is water-soluble, water-dispersible, or both, comprising a polymer main chain and polyester side-arms which contain sulfonic acid groups and which are linked to said polymer main chain via ester groups, wherein said side-arms have been at least partially neutralized by sodium and lithium cations, wherein the molar ratio of lithium to sodium is between 0.1 and 50.

2. The comb polymer according to claim 1, wherein the molar ratio of lithium to sodium is between 0.5 and 25.

3. The comb polymer according to claim 1, wherein the polymer main chain comprises at least one polymer selected from the group consisting of polyacrylic acid, polymethacrylic acid, esters of polyacrylic acid, esters of polymethacrylic acid, polymaleic acid, polymaleic anhydride, and polyfumaric acid.

4. The comb polymer according to claim 1, wherein the polymer main chain comprises at least one ester of polyacrylic acid or polymethacrylic acid with a $C_1$ to $C_{22}$ aliphatic, cycloaliphatic or aromatic alcohol.

5. The comb polymer according to claim 1, wherein the polyester side-arms comprise at least one polyester selected from the group consisting of:

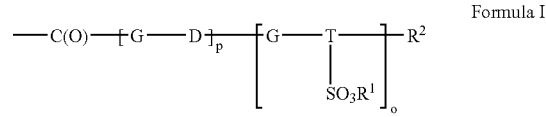

Formula I

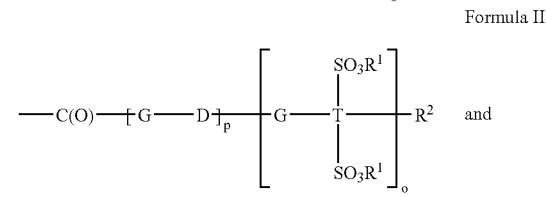

Formula II and

-continued

Formula III

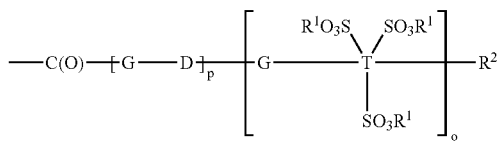
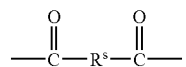

wherein:
p and o represent the number of repeating monomer units;
G is selected from the group consisting of $C_2$ to $C_{22}$ aromatic, aliphatic and cycloaliphatic organyl units containing at least two terminal oxygen atoms and derivatives of a polyglycol of the formula $HO-[R^3-O]_{k'}-[R^4-O]_{m'}-H$, corresponding to an organyl unit

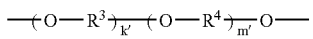

wherein $R^3$ and $R^4$ are each $C_2$–$C_{22}$ alkylene radicals, and are the same or different and $k'+m' \geq 1$;
D is selected from the group consisting of $C_2$ to $C_{22}$ aromatic, aliphatic and cycloaliphatic organyl units containing at least two terminal acyl groups;
T is selected from the group consisting of sulphonated aromatic, aliphatic and cycloaliphatic organyl radicals containing at least two terminal acyl groups;
at least some of said $R^1$ are lithium and sodium cations, and optionally at least some of said $R^1$ are cations different from lithium and sodium cations; and
$R^2$ is selected from the group consisting of:
aromatic, aliphatic and cycloaliphatic amino functional radicals including a $-NH-R^5$ or $-NR^5_2$ group, wherein $R^5$ is selected from the group consisting of $C_1$ to $C_{22}$ alkyl and aryl radicals;
aromatic, aliphatic and cycloaliphatic organyl radicals bridged via ether functions $-O-R^5$, wherein $R^5$ is the same as defined above;
mono- or polyethoxylated sulphonated organyl radicals having the formula $-(O-CH_2-CH_2)_s-SO_3R^1$, wherein $s \geq 1$; and
polyalkoxy compounds bridged via ether functions of the formula $-O-[R^7-O]_q-[R^8-O]_r-Y$, wherein $R^7$ and $R^8$ are each independently selected from the group consisting of $C_2$ to $C_{22}$ alkyl radicals and are the same or different, Y is hydrogen or a $C_1$–$C_{22}$ aliphatic radical, and $q+r \geq 1$.

6. The comb polymer according to claim 5, wherein said one or more additional cations of $R^1$ are selected from the group consisting of potassium, magnesium, calcium, ammonium, monoalkylammonium, dialkylammonium, trialkylammonium and tetraalkylammonium, wherein the alkyl positions of the ammoniums, independently of one another, comprise a $C_1$ to $C_{22}$-alkyl radical and 0 to 3 hydroxyl groups.

7. The comb polymer according to claim 5, wherein D comprises an organyl unit of the formula:

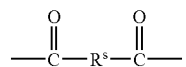

wherein $R^S$ is a $C_2$ to $C_{22}$ aromatic, linear or cyclic, saturated or unsaturated, aliphatic bifunctional radical.

8. The comb polymer according to claim 7, wherein D is derived from a dicarboxylic acid monomer selected from the group consisting of phthalic acid, isophthalic acid, naphthalenedicarboxylic acid, cyclohexanedicarboxylic acid, adipic acid, succinic acid, glutaric acid, pimelic acid, suberic acid, azelaic acid, sebacic acid, brassylic acid, and combinations thereof.

9. The comb polymer according to claim 1, wherein said polymer has a number average molecular weight from 200 to 2,000,000 g/mol.

10. The comb polymer according to claim 9, wherein said polymer has a number average molecular weight from 200 and 100,000 g/mol.

11. The comb polymer according to claim 10, wherein said polymer has a number average molecular weight from 1,000 to 30,000 g/mol.

12. The comb polymer according to claim 11, wherein said polymer has a number average molecular weight from 5,000 to 15,000 g/mol.

13. The comb polymer according to claim 5, wherein said polymer has a number average molecular weight from 200 to 2,000,000 g/mol.

14. The comb polymer according to claim 13, wherein said polymer has a number average molecular weight from 200 and 100,000 g/mol.

15. The comb polymer according to claim 14, wherein said polymer has a number average molecular weight from 1,000 to 30,000 g/mol.

16. The comb polymer according to claim 15, wherein said polymer has a number average molecular weight from 5,000 to 15,000 g/mol.

17. A cosmetic preparation comprising a comb polymer according to claim 1 and one or more cosmetic auxiliaries.

18. The cosmetic preparation according to claim 17, wherein the cosmetic preparation is a hair-setting composition, a shampoo, or a lotion.

19. The cosmetic preparation according to claim 18, wherein the cosmetic preparation is a hair-setting composition in the form of a spray, foam aerosol, or gel.

20. The cosmetic preparation according to claim 19, wherein the comb polymer is present at a concentration of 0.5 to 30 weight percent.

* * * * *

UNITED STATES PATENT AND TRADEMARK OFFICE
CERTIFICATE OF CORRECTION

PATENT NO. : 7,129,299 B2 Page 1 of 1
APPLICATION NO. : 10/826669
DATED : October 31, 2006
INVENTOR(S) : Detert et al.

It is certified that error appears in the above-identified patent and that said Letters Patent is hereby corrected as shown below:

Column 22,

Lines 26 and 39, "and" should read --to--.

Signed and Sealed this

Tenth Day of April, 2007

JON W. DUDAS
*Director of the United States Patent and Trademark Office*